United States Patent
Chowienczyk et al.

(10) Patent No.: US 10,159,445 B2
(45) Date of Patent: Dec. 25, 2018

(54) METHOD AND APPARATUS FOR MEASURING BLOOD PRESSURE

(71) Applicant: SunTech Medical, Inc., Morrisville, NC (US)

(72) Inventors: Philip Jan Chowienczyk, London (GB); Antoine Yves Marie Guilcher, London (GB); Sally Emma Brett, London (GB); Christopher Patrick Lawson, Kent (GB)

(73) Assignee: SunTech Medical, Inc., Morrisville, NC (US)

( * ) Notice: Subject to any disclaimer, the term of this patent is extended or adjusted under 35 U.S.C. 154(b) by 1006 days.

(21) Appl. No.: 14/354,850

(22) PCT Filed: Oct. 29, 2012

(86) PCT No.: PCT/GB2012/052683
§ 371 (c)(1),
(2) Date: Apr. 28, 2014

(87) PCT Pub. No.: WO2013/061089
PCT Pub. Date: May 2, 2013

(65) Prior Publication Data
US 2014/0316288 A1    Oct. 23, 2014

(30) Foreign Application Priority Data
Oct. 27, 2011    (GB) .................................. 1118644.2

(51) Int. Cl.
*A61B 5/021*    (2006.01)
*A61B 5/00*    (2006.01)
*A61B 5/022*    (2006.01)

(52) U.S. Cl.
CPC .......... *A61B 5/725* (2013.01); *A61B 5/02108* (2013.01); *A61B 5/02116* (2013.01); *A61B 5/02225* (2013.01)

(58) Field of Classification Search
CPC . A61B 5/725; A61B 5/02108; A61B 5/02116; A61B 5/02225
See application file for complete search history.

(56) References Cited

U.S. PATENT DOCUMENTS

| 5,265,011 A | 11/1993 | O'Rourke |
| 5,560,366 A | 10/1996 | Harada et al. |

(Continued)

FOREIGN PATENT DOCUMENTS

| EP | 1179318 | 2/2002 |
| JP | H03231631 | 10/1991 |

(Continued)

OTHER PUBLICATIONS

Guilcher Antoine et al: "Estimating central SBP from the peripheral pulse: influence of waveform analysis and calibration error.", Jul. 2011 (Jul. 2011), Journal of Hypertension Jul. 2011, vol. 29, Nr. 7. pp. 1357-1366.

(Continued)

*Primary Examiner* — Tiffany Weston
(74) *Attorney, Agent, or Firm* — Myers Bigel, P.A.

(57) ABSTRACT

Embodiments of the present invention provide an improved transformation method whereby the peripheral pulse waveform is filtered to separate different phases which make up the waveform. The separate phases are transformed before being re-combined to provide an estimated intra-arterial transfer function. For example, in one embodiment the peripheral pulse waveform is filtered by a first high pass filter, and a copy of the peripheral pulse waveform filtered by a second high pass filter, having a different cut-off (Continued)

frequency. The two filtered waveforms may then be further processed, for example by being added back to original wave-form, and are then multiplexed together in a time division manner to provide a final waveform. For example, the part of the first filtered waveform corresponding to the systolic phase may be combined with the part of the second filtered waveform corresponding to the diastolic phase to produce the final waveform, and the respective filter cut-off frequencies may be chosen to extract characteristics of the respective phases of the heart.

36 Claims, 6 Drawing Sheets

(56) References Cited

U.S. PATENT DOCUMENTS

| | | | | |
|---|---|---|---|---|
| 6,045,510 | A * | 4/2000 | Ogura | A61B 5/02116 600/485 |
| 2002/0177781 | A1 | 11/2002 | Amano | |
| 2003/0023173 | A1 | 1/2003 | Bratteli et al. | |
| 2003/0097074 | A1 | 5/2003 | Oka et al. | |
| 2005/0283087 | A1 | 12/2005 | Takazawa et al. | |
| 2006/0224070 | A1 | 10/2006 | Sharrock et al. | |
| 2006/0264771 | A1 | 11/2006 | Lin et al. | |
| 2008/0306393 | A1 | 12/2008 | Ting et al. | |
| 2009/0149763 | A1 | 6/2009 | Chen et al. | |
| 2012/0157791 | A1 * | 6/2012 | Hersh | A61B 5/02225 600/301 |

FOREIGN PATENT DOCUMENTS

| | | |
|---|---|---|
| JP | 2004-121866 | 4/2004 |
| JP | 2005-278965 | 10/2005 |
| WO | WO2006/072776 | 7/2006 |
| WO | WO2009/139646 | 11/2009 |
| WO | 2010058169 A1 | 5/2010 |
| WO | WO 2010/058169 * 5/2010 | A61B 5/022 |

OTHER PUBLICATIONS

Jin-Oh Hahn et al: "A new approach to reconstruction of central aortic blood pressure using a adaptivea transfer function", Engineering in Medicine and Biology Society. 2008. EMBS 2008. 30th Annual International Conference of the IEEE. IEEE, Piscataway, NJ. USA, Aug. 20, 2008 (Aug. 20, 2008), pp. 813-816.
Wassertheurer S et al: "A new oscillometric method for pulse wave analysis: comparison with a common tonometric method.", Aug. 2010 (Aug. 2010), Journal of Human Hypertension Aug. 2010, vol. 24, Nr. 8, pp. 498-504.
International Search Report issued in corresponding International Application No. PCT/GB2012/052683, dated Feb. 11, 2013.
Brett et al., Estimating central systolic blood pressure during oscillometric determination of blood pressure: proof of concept and validation by comparison with intra-aortic pressure recording and arterial tonometry, Blood Pressure Monitoring, 2012, pp. 132-136, vol. 17, No. 3.
Karamanoglu et al., On-line Synthesis of the Human Ascending Aortic Pressure Pulse From the Finger Pulse, Hypertension, 1997, pp. 1416-1424, vol. 6, No. 30.
Miyashita et al., Aging and Arterial Pressure Waveform—Augmentation Index, Modern Physician, 2004, pp. 1699-1704, vol. 24, No. 11.
O'Rourke et al. Pulse wave analysis, Journal of Hypertension, 1996, pp. S147-S157, vol. 14, Suppl 5.
Yaginuma et al., Genesis of the Arterial Pressure Waveform and Transmission Changes to Measurement Points, Blood Pressure, 2001, pp. 1035-1040, vol. 8, No. 10.

* cited by examiner

METHOD AND APPARATUS FOR MEASURING BLOOD PRESSURE

TECHNICAL FIELD

The present invention relates to a method and an apparatus for measuring and estimating the blood pressure of a subject and more specifically relates to a method and an apparatus for estimating the intra-arterial blood pressure waveform of a subject.

BACKGROUND TO THE INVENTION

Blood pressure (BP) refers to the force exerted by circulating blood on the walls of blood vessels, and constitutes one of the principal vital signs. The pressure of the circulating blood decreases as blood moves through arteries, arterioles, capillaries, and veins. The term blood pressure generally refers to arterial pressure, i.e., the pressure in the larger arteries. Arteries are the blood vessels which take blood away from the heart.

Blood pressure in the arteries changes in a generally oscillatory manner and can be displayed as a waveform (a graph of pressure against time). The peak pressure in the arteries is known as the systolic blood pressure (SBP) and occurs near the beginning of the cardiac cycle. The lowest pressure in the arteries, which occurs at the resting phase of the cardiac cycle, is known as the diastolic blood pressure (DBP). The average pressure throughout the cardiac cycle is known as the mean arterial pressure (MAP), and the pulse pressure (PP) is the difference between the systolic and diastolic pressures.

Existing blood pressure monitors provide a measure of systolic and diastolic blood pressure in the peripheral arteries, e.g. the arm. However, it has long been recognised that systolic blood pressure measured at the brachial artery, radial artery or digital artery exceeds central systolic blood pressure (cSBP) at the aortic root because systolic blood pressure is amplified above that close to the heart by propagation along the peripheral arteries in the upper limb as a result of reflected pressure waves. This also results in a difference in the central pulse pressure compared to the peripheral pulse pressure. Diastolic blood pressure is similar at central and peripheral sites because of the slow rate of change of pressure during diastole.

Mean arterial pressure is also similar at central and peripheral sites. cSBP would be expected to provide a better indication of the load on the heart and hence be more closely related to heart disease than peripheral systolic blood pressure (pSBP).

Blood pressure is usually measured in the upper arm by an oscillometric method using a cuff inflated around the upper arm. Pressure in the cuff is inflated to a pressure above systolic blood pressure in the arm (peripheral systolic blood pressure, pSBP) and then slowly deflated to a pressure below diastolic blood pressure in the arm (DBP). At any time during the deflation, when mean cuff pressure (MCP) during one cardiac cycle falls below pSBP, cuff pressure oscillates by a small amount around MCP. pSBP and DBP can be estimated from the amplitude of pressure oscillations within the cuff.

It is known that, whilst the mean arterial blood pressure (MAP) and DBP differ little between the aorta and conduit arteries in the arm, pSBP measured in the upper limb is amplified above central systolic blood pressure in the aorta (cSBP) by propagation along the upper limb which results in amplification due to reflections. cSBP is thought to provide a better estimate of the risk of a cardiovascular event than pSBP. Furthermore, when comparing antihypertensive drug regimes that have similar effects on pSBP but differential effects on cSBP, lower cSBP was associated with improved outcome. There is therefore a demand for methods of non-invasive estimation of cSBP.

The most commonly employed method involves the measurement of a peripheral blood pressure waveform from the radial artery by applanation tonometry (holding a pressure sensor over the radial artery to gently compress it against underlying bone). This pressure waveform may then be calibrated from oscillometric measurements of pSBP and DBP. A "generalised transfer function" (GTF) is then applied to this peripheral cuff pressure waveform to transform it into a central waveform from which cSBP can be estimated. The GTF can be derived either in the frequency domain using fast Fourier transforms or in the time domain using a parametric function. The GTF exploits the fact that, for a given shape or frequency content of the central waveform, the upper arm exerts a relatively constant influence on the waveform irrespective of age and other intra-individual characteristics. Applanation tonometry requires is performed by a trained observer, takes several minutes to perform, requires relatively expensive equipment, and requires an oscillometric or other measurement of blood pressure.

An advance on the tonometry based methodology derives a blood pressure waveform direct from an upper arm cuff used for oscillometric measurement of blood pressure. When the cuff is inflated (usually to a pressure between DBP and pSBP), pressure waveforms recorded from the cuff bear some resemblance to those within the artery within the arm (and those obtained by tonometry). The cuff can be inflated to a suprasystolic pressure (above pSBP) but this is uncomfortable for the patient and also means that the method is more difficult to apply during the routine oscillometric measurement of blood pressure. During such a measurement an objective is to minimise the time at which cuff pressure exceeds pSBP in order to maximise the information on cuff pressure oscillations during deflation from pSBP to DBP.

The GTF used for transforming a tonometer derived peripheral waveform to a central waveform cannot be used to transform the cuff waveform to a central waveform. An alternative GTF may, however, be used to transform the cuff waveform to a central waveform. The characteristics of the GTF are dependent on the mean pressure within the cuff during the acquisition of the cuff waveform. Because the cuff waveform differs from an intra-arterial or tonometer derived waveform, it cannot be calibrated from pSBP and DBP.

The central waveform derived from applying a GTF to the cuff waveform can be calibrated from the MAP and DBP because of the equality of MAP and DBP at central and peripheral sites. MAP and DBP values may be obtained by an oscillometric method.

The above methodology, therefore, allows cSBP to be determined from a blood pressure cuff during (or immediately before or after) the conventional measurement of oscillometric blood pressure and in a manner that imposes no more onerous requirements on the patient or observer than the conventional measurement of blood pressure. A first disadvantage with this blood pressure cuff approach is the requirement to calibrate the waveform from MAP and DBP. There is at present no agreed standard for validating the accuracy of MAP as derived by an oscillometric method. A second disadvantage is that calibration from MAP and DBP may be influenced to a greater degree by errors in estimation of DBP by the oscillometric method. Conversely, if a calibration by pSBP and DBP is performed, errors in estimation of pSBP give rise to a similar error in cSBP. Thus, even if the oscillometric method is subject to some error, the difference between the estimated cSBP and pSBP remains an accurate measure of the difference between the true cSBP and pSBP.

Calibration of a cuff derived waveform by pSBP and DBP, prior to transformation to a central waveform, is relatively inaccurate compared to when a similar procedure is applied to a tonometer derived waveform. This is because, unlike the tonometer derived waveform, the shape and form of the cuff waveform do not bear a constant relationship to that of the true intra-arterial pressure waveform. The cuff waveform is distorted by an amount dependent on the difference between the MCP and the intra-arterial pressure and on the phase of the cardiac cycle. A closer approximation to intra-arterial pressure is obtained by inflating the cuff to a pressure above pSBP, but this has the disadvantages discussed above.

One method of transforming a peripheral pulse waveform measured using an oscillometric method, i.e. gained using a cuff pressure device, into a corresponding intra-arterial waveform uses a general transfer function. This method is not fully accurate, thus there is motivation to improve the accuracy of the method of transforming a peripheral pulse waveform into an intra-arterial waveform.

SUMMARY OF INVENTION

Embodiments of the present invention provide an improved transformation method whereby the peripheral pulse waveform is filtered to separate different phases which make up the waveform. The separate phases are transformed before being recombined to provide an estimated intra-arterial transfer function. For example, in one embodiment the peripheral pulse waveform is filtered by a first high pass filter, and a copy of the peripheral pulse waveform filtered by a second high pass filter, having a different cut-off frequency. The two filtered waveforms may then be further processed, for example by being added back to original waveform, and are then multiplexed together in a time division manner to provide a final waveform. For example, the part of the first filtered waveform corresponding to the systolic phase may be combined with the part of the second filtered waveform corresponding to the diastolic phase to produce the final waveform, and the respective filter cut-off frequencies may be chosen to extract characteristics of the respective phases of the heart.

According to a first aspect of the invention, there is provided a method of processing a peripheral pulse waveform derived from an oscillometric measurement to estimate a corresponding intra-arterial waveform, the method comprising filtering the peripheral pulse waveform with respective filters to provide a plurality of waveforms, and time division multiplexing the plurality of waveforms to provide a combined waveform representing the estimated intra-arterial waveform.

Using an oscillometric measurement allows the data to be collected using a simple device requiring a low skill level, which makes it suitable for use by untrained staff and for automated patient home monitoring. Multiplexing the waveforms in the time domain allows the individual waveforms to be recombined without cross-interference.

The peripheral pulse waveform may be filtered at a first frequency to provide a first filtered waveform and at a second frequency to provide a second filtered waveform, and the first frequency is associated with a first phase of a cardiac cycle and the second frequency is associated with a second phase of the cardiac cycle.

At least one of the plurality of waveforms may be transformed prior to being combined and, optionally, amplified prior to being combined. The filtered waveforms may require amplification to best reconstruct its corresponding intra-arterial waveform. The amplification may be positive or negative.

The first phase may be a systolic phase of the cardiac cycle or a sharp upstroke beginning a systolic phase of the cardiac cycle. The second phase may be a diastolic phase of the cardiac cycle. By using the above aspect of the invention to isolate specific components of the cardiac cycle, the separate components can be separately transformed to estimate the corresponding intra-arterial waveform.

The first frequency may be a frequency between 3 Hz and 20 Hz and preferably approximately 3.2 Hz. These frequencies are associated with the systolic phase of the cardiac cycle. The second frequency may be a frequency between 1.5 Hz and 20 Hz and preferably approximately 1.75 Hz. These frequencies are associated with the diastolic phase of the cardiac cycle.

The peripheral pulse waveform is filtered by a first high pass filter to provide the first filtered waveform and a second high pass filter to provide the second filtered waveform. If an individual filter is used to filter specific frequencies, the individual filter may be tuned more easily.

The first filter may be a higher order than the second filter. This arrangement allows filtering of multiple frequencies while also minimising the complexity of an arrangement providing the circuitry or software. The first filter may be a seventh order filter and the second filter may be a fourth order filter. Such orders of filters have been found to be of particular benefit in implementing the invention.

The combined waveform may be smoothed using a smoothing filter. Preferably, the smoothing filter attenuates frequencies above 20 Hz. The smoothing filter may be a low-pass filter with a cut-off frequency of approximately 6 Hz. The smoothing filter removes unwanted parts of the combined waveform which are introduced when the first and second filtered waveforms are combined. The frequencies of most interest are below 20 Hz, while 6 Hz has been found to be a preferable cut-off frequency providing the best response for the filter.

The smoothing filter may be of a lower order than the first and second filters. This allows for a simpler implementation of the invention, while maintaining the accuracy of the estimate intra-arterial waveform. A third order filter has been shown to be useful as a smoothing filter by providing a suitable frequency response.

The combined waveform may be a complete cardiac cycle. This enables more information to be gained from the waveform.

The intra-arterial cardiac waveform may be used to estimate an accurate intra-arterial mean arterial blood pressure (MAPavwave). It is possible to achieve an accurate MAPavwave using only oscillometric measurements taken from the subject using a cuff measurement device using peripheral blood pressure measurements.

The estimation of the MAPavwave requires pSBP and DBP in order to calibrate a central waveform. This is possible by transforming a cuff waveform into an intra-arterial waveform (as performed by the present invention). This intra-arterial waveform can then be calibrated from pSBP and DBP and used to obtain MAPavwave as the average of this intra-arterial waveform. This does not rely on an oscillometric method for estimating MAP, but on the systolic and diastolic pressures obtained by the oscillometric method. The original peripheral cuff waveform can then be transformed to a central aortic waveform and calibrated from MAPavwave and DBP.

According to a second aspect of the invention, there is provided an apparatus for processing a peripheral pulse waveform derived from an oscillometric measurement to estimate a corresponding intra-arterial waveform, the apparatus comprising an input for receiving the peripheral pulse waveform; a first filter arranged to filter the peripheral pulse waveform at a first frequency to provide a first filtered waveform; a second filter arranged to filter peripheral pulse waveform at a second frequency to provide a second filtered waveform; a time division multiplexer; and an output for outputting the estimated intra-arterial waveform; wherein the for multiplexer combines the first and second filtered waveforms to produce the estimated intra-arterial waveform.

The first frequency may be between 3 Hz and 20 Hz, but, preferably, approximately 3.2 Hz. The second frequency may be between 1.5 Hz and 20 Hz, but, preferably, approximately 1.75 Hz. The first and second filters may be high pass filters and the first filter may be of a higher order than the second filter. The apparatus may further comprise a smoothing filter to filter the output waveform. Any smoothing filter may attenuates frequencies above 20 Hz and, in particular, the smoothing filter may be a low-pass filter with cut-off frequency of approximately 6 Hz. The advantages of these features correspond to the advantages of the above corresponding method features.

The time divided multiplexer may also combine an unfiltered peripheral pulse waveform with the first and second filtered waveforms. This allows for a better reconstruction of the estimated intra-arterial waveform using parts of the original peripheral pulse waveform.

The filters are explicitly recited as being Butterworth filters in at least one aspect of the present invention as they provide a suitable phase and frequency response. Other types of filters may be used to replace one or all of the filters of any aspect or embodiment of the invention, or in addition to any of the filters of any of the embodiments of the invention. Such other types of filters include analogue filters including passive and active filters, and digital filters implemented using electronic components or software filters implemented using a microprocessor. Examples of other filters include Chebyshev type filters, Bessel type filters, and Elliptic type filters. The chosen orders of the filters have been found to be particularly suitable, however, other orders of filters may be used.

DESCRIPTION OF THE DRAWINGS

Embodiments of the invention shall now be described, by way of example only, with reference to accompanying drawings, in which.

DESCRIPTION OF EMBODIMENTS

Embodiments of the invention will now be described.

Figure 1:
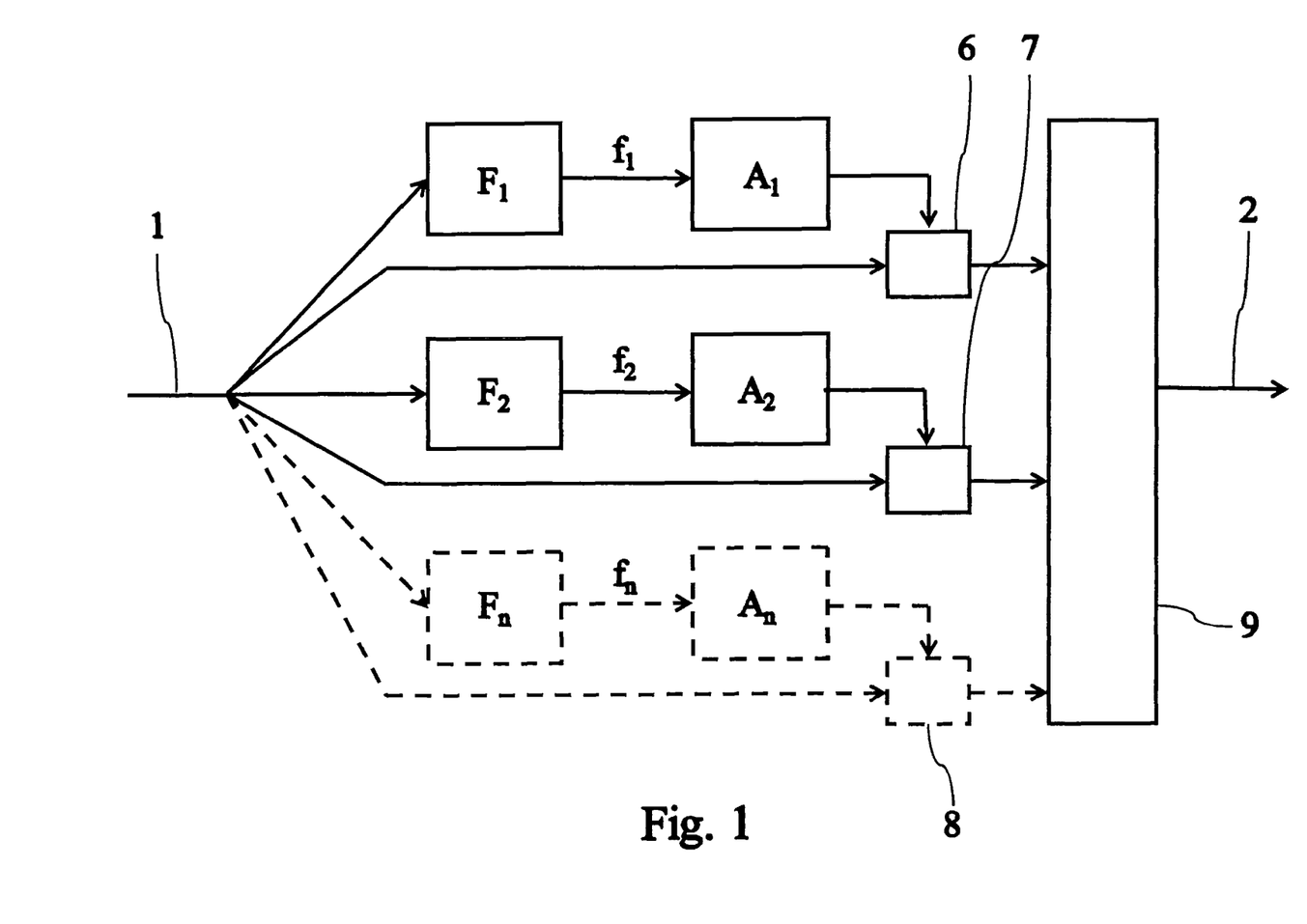
FIG. 1 shows a block diagram of one embodiment of the invention.

FIG. 1 shows a signal processing block diagram which accepts a peripheral pulse waveform as an input 1 and provides an estimated corresponding intra-arterial waveform as an output 2. Three filters $F_1$, $F_2$, $F_n$ are shown accepting the input 1. One of the filters $F_n$ and its associated components $A_n$, 8 are optional and this is denoted by them being drawn using broken lines. Each filter $F_1$, $F_2$, $F_n$ is tuned to a different frequency associated with a specific phase of the peripheral pulse waveform. The output signal of each filter $f_1$, $f_2$, $f_n$ is amplified and each of the amplified filter output signals is added to the input signal. An amplifier $A_1$, $A_2$, $A_n$ may amplify its associated filter output $f_1$, $f_2$, $f_n$ with a gain greater, equal or less than 1. The amplified filter output is combined with the input signal using components 6, 7, 8. The outputs of the combining components are reconstructed to form an estimated intra-arterial waveform at the output 2. The output signal will correspond to the input signal, however, each component of the input waveform corresponding to a specific phase of the pulse waveform will be transformed by the filtration and amplification process.

The optional components and connections of FIG. 1 may be included to provide three filtered paths. This embodiment of the invention may also include other filtered paths in addition to the optional filter path shown. Each filter path, including those shown and those described as being additional to those shown, is arranged to filter and amplify a specific phase of the peripheral phase waveform input to the signal processing circuit. The amplifiers $A_1$, $A_2$, $A_n$ are shown as being separate to the filters $F_1$, $F_2$, $F_n$, but may in fact be combined with the filters to, whereby each filter $F_1$, $F_2$, $F_n$ is arranged to also provide a gain.

An additional filter (not shown) may be provided at the output 2 the signal processing circuit. This additional filter is be arranged to smooth the reconstructed signal provided at the output 2.

Figure 2A:
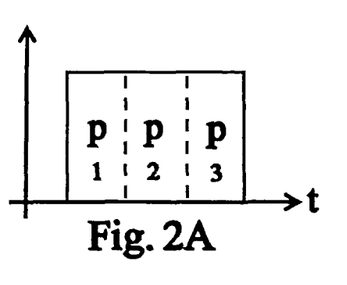
FIGS. 2A to 2E show a method of combining signals in accordance with an embodiment of the invention.

The filtered and amplified signals of FIG. 1 may be reconstructed by mixing or by multiplexing. FIGS. 2A to 2E illustrate how such a modulation process works. FIG. 2A illustrates an example input signal provided at the input 1 of FIG. 1. The vertical axes of each of the graphs of FIGS. 2A to 2E represent magnitude of an input signal and the horizontal axes represent time.

FIG. 2A shows the input signal divided into three phases $p_1$, $p_2$, $p_3$. Each phase $p_1$, $p_2$, $p_3$ corresponds to a phase of the peripheral pulse waveform. Each phase $p_1$, $p_2$, $p_3$ will have a different frequency characteristic compared to the other phases which are specific to that particular phase.

Figure 2B:
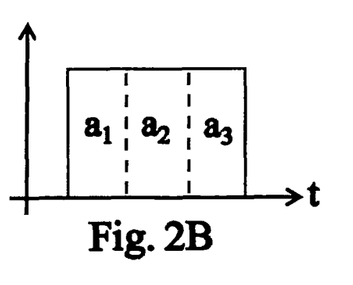
Figure 2C:
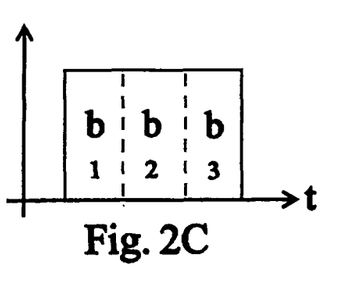
Figure 2D:
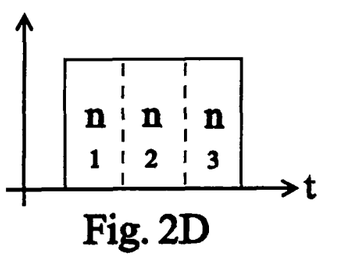
Figure 2E:
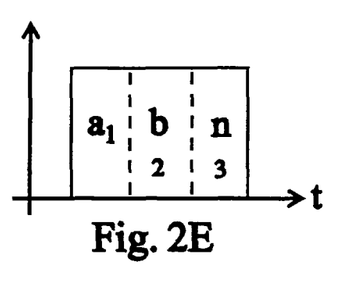

FIGS. 2B, 2C and 2D represent respective signal outputs from the combining modules 6, 7, 8 of FIG. 1. The output of combining component 6 is illustrated in FIG. 2B; the output of combining component 7 is illustrated by FIG. 2C; and the output of combining component 8 is illustrated by FIG. 2D. The outputs are different for each combining component 6, 7, 8 because of the different filtering and amplification characteristics of each filter and amplifier pair. The combined output signals are reconstructed by reconstruction block 9 which, in this embodiment, creates an estimated intra-arterial waveform by multiplexing the outputs. The output 2 of the reconstruction block 9 is illustrated in FIG. 2E. The signal of FIG. 2E, like the signals of FIGS. 2A to 2D, has three phases $a_1$, $b_2$, $n_3$, whereby each phase is provided by a different filter-amplifier pair. This process of multiplexing may be repeated indefinitely to provide continuous waves at the output 2 of the signal processing circuit of FIG. 1. The number of paths in the signal processing apparatus of FIG. 1 may be increased and the number of separate phases in the peripheral pulse waveform which may processed separately before being reconstructed into an stimulated intra-arterial waveform would increase correspondingly.

A filter receiving the output of the reconstruction block 9 may be included. This filter would smooth out any discontinuity between the multiplexed signal output.

Figure 3:
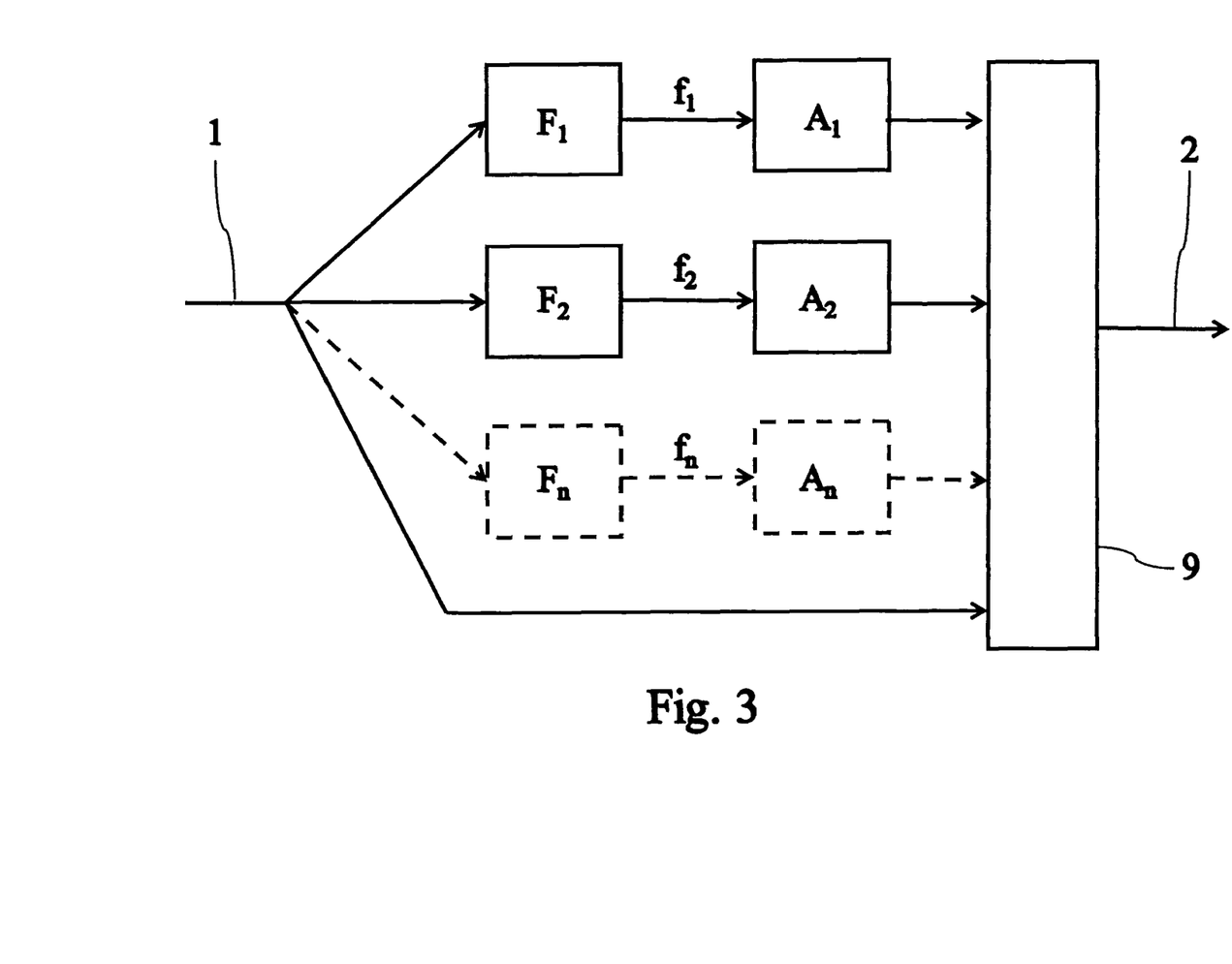
FIG. 3 shows a block diagram of another embodiment of the invention.

FIG. 3 illustrates an embodiment of a signal processing circuit similar to that shown in FIG. 1. Blocks and features with functions corresponding to those of FIG. 1 are numbered identically. In this embodiment, the outputs of the amplifiers $A_1$, $A_2$, $A_n$ are combined with the original input 1 by the reconstruction block 9. Unlike the circuit of FIG. 1, that of FIG. 9 has an additional connection coupling the input 1 to the reconstruction block 9.

Figure 4:
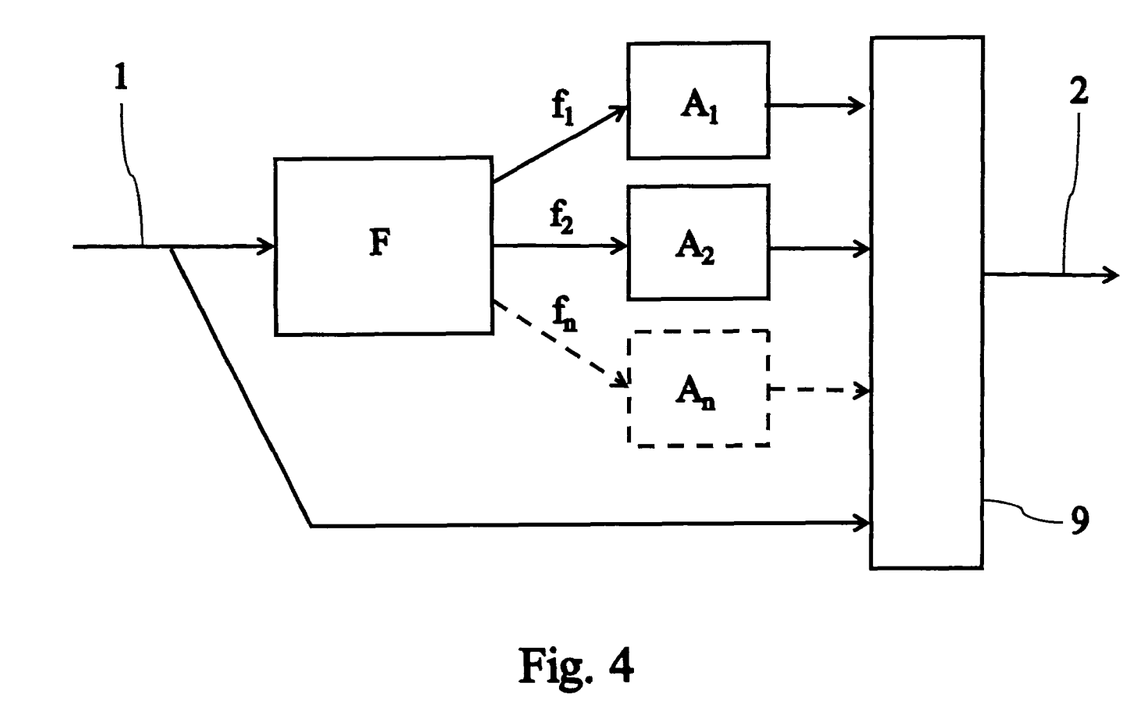
FIG. 4 shows a block diagram of a further embodiment of the invention.

FIG. 4 illustrates another embodiment of a signal processing circuit in accordance with an embodiment of the invention which utilises a more complex filter F. The filter F receives an input signal from the input 1 and outputs a plurality of signals $f_1$, $f_2$, $f_n$ which are then amplified. In this embodiment, only a single filter is required. The filter F may be an electronic filter programmed by software. Although each filtered signal is shown as being amplified by separate amplifiers $A_1$, $A_2$, $A_n$, the amplification of the filtered signals $f_1$, $f_2$, $f_n$ may be provided by the filter F. The filtered and amplified signals and the original unfiltered signal are then reconstructed by the reconstruction block 9.

Figure 5:
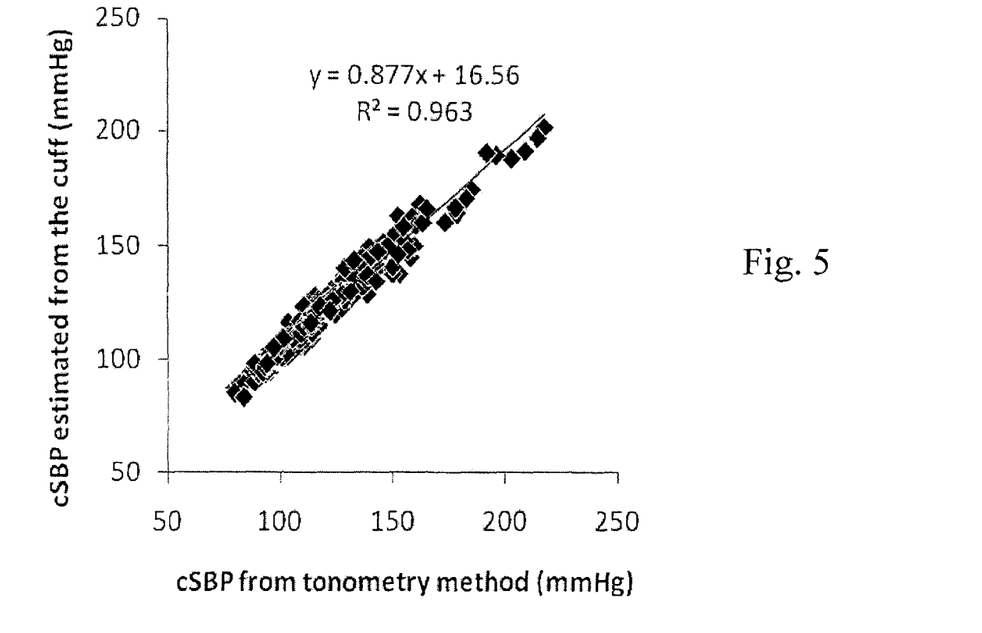
FIG. 5 shows a simple linear regression of results of a method of the prior art.
Figure 6:
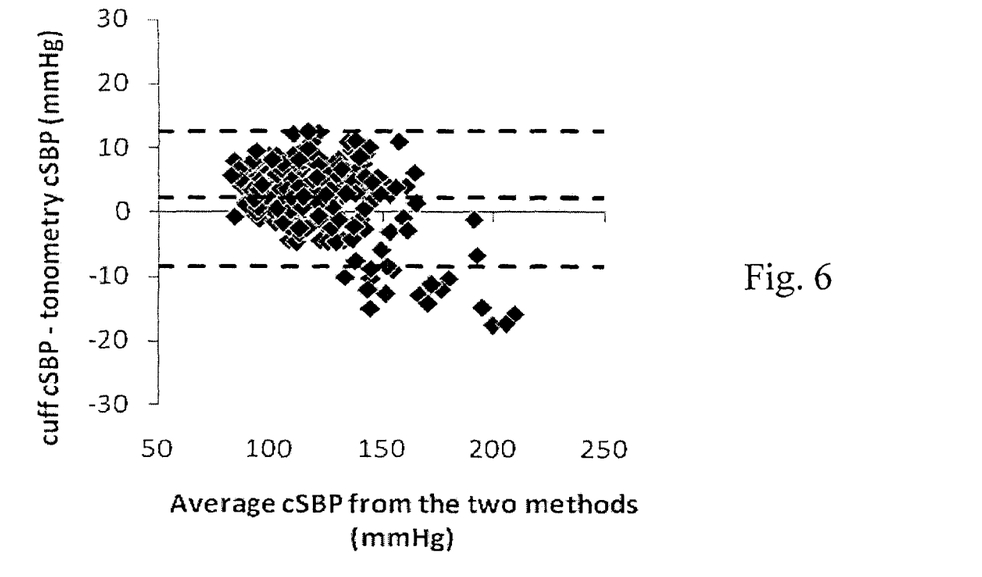
FIG. 6 shows a graph of the mean and standard deviation of the data set of FIG. 5.

FIGS. 5 and 6 show a comparison between cSBP estimated from a cuff waveform and cSBP estimated from a tonometry waveform with the cuff waveforms calibrated by (1) using a GTF to first transform this waveform to a local peripheral intra-arterial waveform, (2) calibrating the local peripheral intra-arterial waveform with oscillometric measurements of pSBP and DBP, (3) obtaining MAPavwave from this calibrated local peripheral intra-arterial waveform and, (4) using MAPavwave and DBP to calibrate a central blood pressure waveform obtained from transforming the original cuff waveform.

FIG. 6 shows a mean difference (±SD) of 2.2 (±5.2) mmHg between cSBP estimated from the cuff and cSBP estimated from the tonometry method. The upper and lower dashed lines of the figure represent the mean difference ±(double the SD), i.e. ±10.4.

This approach is shown to be of lower accuracy than an alternative approach. This is likely to be due to distortion of the cuff waveform differing within the phases of the cardiac cycle. Regional (e.g. central versus peripheral) changes in an intra-arterial waveform mainly occur during the systolic phase with the diastolic phase remaining primarily as an exponential decay, while deviation of a cuff waveform from an intra-arterial waveform also occurs during diastole. This unpredictable deviation of the cuff waveform during diastole impairs the accuracy of the transformation of a cuff waveform to an intra-arterial waveform when using a GTF, especially for the reconstruction of the diastolic phase.

Figure 7:
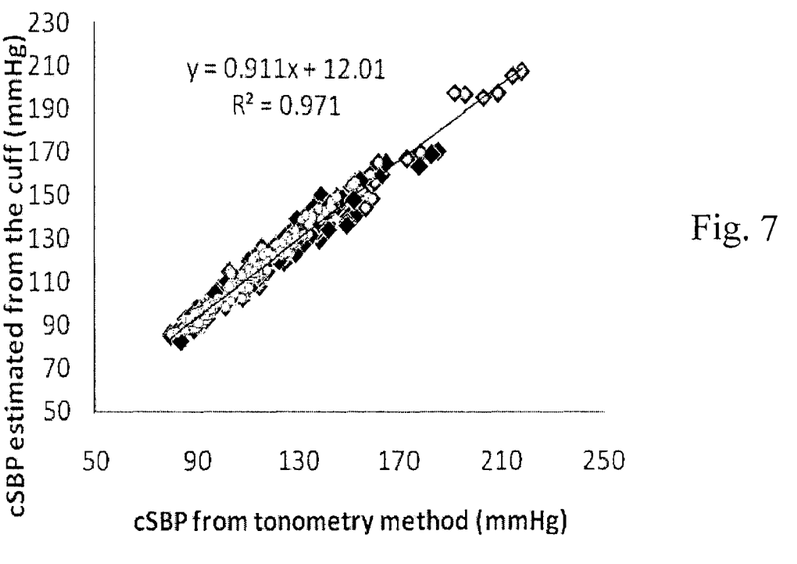
FIG. 7 shows a simple linear regression graph of the results of an example method carried out in accordance with an embodiment of the present invention compared to a method of the prior art.
Figure 8:
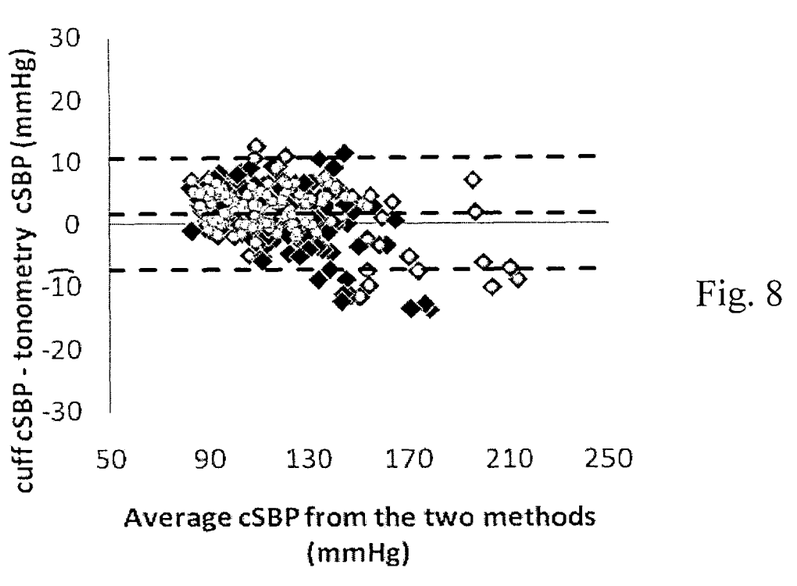
FIG. 8 shows a graph of the mean and standard deviation of the data set of FIG. 8.

FIGS. 7 and 8 show the results of an example of a method in accordance with the preferred method of transforming a cuff waveform to a local intra-arterial waveform as in the embodiment of the present invention. The method uses a cuff pressure measurement which has been gathered from a subject to reconstruct an arterial pulse waveform by extracting systolic and diastolic waveform phases from the cuff pressure waveform.

FIG. 7 shows a mean difference (±SD) of 1.62 (±4.47) mmHg between cSBP estimated from the cuff and cSBP estimated from the tonometry method. The upper and lower dashed lines of the figure represent the mean difference ±(double the SD), i.e. ±8.94.

Specifically, FIGS. 7 and 8 show a comparison between cSBP estimated from a cuff waveform and cSBP estimated from a tonometry waveform by (1) using the time division multiplexing method described below to transform the cuff waveform to a local peripheral intra-arterial waveform, (2) calibrating the local peripheral intra-arterial waveform with oscillometric measurements of pSBP and DBP, (3) obtaining MAPavwave from this calibrated local peripheral intra-arterial waveform, and (4) using MAPavwave and DBP to calibrate a central blood pressure waveform obtained from transforming the original cuff waveform.

A specific embodiment of the present invention will now be described, in terms of the specific example processing performed, and the results obtained.

Method

A first filter is applied to a cuff pressure waveform A in order to extract high frequency features which occur during a systole phase which are necessary to reconstruct the sharp upstroke of a peripheral intra-arterial pulse occurring during the systole phase. The result of the filtering is Waveform B.

Waveform B is amplified and added to waveform A to obtain waveform C. Waveform C is a cuff waveform reconstructed to incorporate high frequency components in the systolic phase of the intra-arterial waveform which are lost in the cuff waveform.

A second filter is applied to the cuff pressure waveform A in order to extract high frequency features necessary to reconstruct the diastolic part of the peripheral intra-arterial pulse. The result of the filtering is Waveform D.

Waveform D is amplified and added to waveform A to obtain waveform E. Waveform E is a cuff waveform reconstructed to incorporate an exponential decay and a possible diastolic peak in the diastolic phase of the intra-arterial waveform which are lost in the cuff waveform.

Pulse waveforms C and E are merged together to obtain a reconstructed arterial pulse. The systolic part of pulse C is used to re-construct the systolic part of the peripheral intra-arterial pulse and the diastolic part of pulse E to reconstruct the diastolic part of the peripheral intra-arterial pulse.

A third filter is then applied to remove any point of discontinuity in the reconstructed arterial pulse. The third filter is preferably a zero phase filter.

EXAMPLE

The following example was conducted in accordance with the above method. The example method and the tonometry method described in the introduction were performed on data gathered from 100 subjects. Three measurements were obtained from each subject using both methods.

The example used a single MCP equal to MAP plus 50% of the difference between MAP and pSBP and sequential filtering applied to two phases of the cardiac cycle, sytstole and diastole.

A seventh order Butterworth filter with a cut-off frequency 3.2 Hz was used as the first filter to identify the highest frequencies during systole. The highest frequencies components of the systolic phase were amplified by a factor of 1.75 before being fed back to the original pulse.

A Butterworth filter of the fourth order with a cut-off frequency of 1.75 Hz was used as the second filter to identify the highest frequencies during diastole. The highest frequencies components of the diastolic phase were added to the original pulse.

The systolic and diastolic phases of the two pulses resulting from the two separate filtering operations were merged into a single pulse.

The third filter was a Butterworth low pass filter of the third order with a cut off frequency of 6 Hz.

Results

In FIGS. 7 and 8, the white dots represent a set of data used to derive the filter characteristics of the example. The black diamonds represent a set of data used to validate the method (this set of data included the set of data used to derive the filter characteristics, hence some of the diamonds in the figures have corresponding circles plotted on them).

A close relationship can be seen between cSBP estimated from the cuff pressure waveforms and cSBP obtained via the tonometry method when both types of waveforms are calibrated using oscillometric values of pSBP and DBP.

Various modifications may be made to the above described embodiments, whether by way of addition, substitution, or deletion, and which are intended to fall within the scope of the appended claims. For example, in one alternative embodiment the peripheral pulse waveform may be time divided into its different phases, such as the systolic phase and the diastolic phase prior to any filtration or other signal processing being applied thereto. The respective divided phase signals may then be processed as required, for example by being appropriately filtered, before then being recombined in a multiplex fashion.

The invention claimed is:

1. A method of estimating an intra-arterial waveform, the method comprising:
   providing a peripheral pulse waveform of a subject to a signal processing circuit comprising at least first and second filters, wherein the peripheral pulse waveform is derived from an oscillometric measurement or measurements of the subject obtained by a blood pressure cuff;
   filtering the peripheral pulse waveform with the at least first and second filters to isolate specific different phases of a cardiac cycle into a plurality of different waveforms including at least first and second ones of the plurality of different waveforms; and then
   electronically time division multiplexing the plurality of different waveforms by selectively combining the plurality of different waveforms to form different portions of a combined waveform according to the phases of the cardiac cycle to represent the estimated intra-arterial waveform.

2. The method of claim 1, wherein the peripheral pulse waveform is filtered by the first filter at a first frequency to provide a first filtered waveform and at a second frequency by the second filter to provide a second filtered waveform as the first and second ones of the plurality of different waveforms, and wherein the first frequency is associated with a first phase of a cardiac cycle and the second frequency is associated with a second different phase of the cardiac cycle and each of the first and second phases has a different frequency characteristic.

3. The method claim 1, wherein at least one of the plurality of different waveforms is transformed prior to being combined.

4. The method of claim 2, wherein at least one of the plurality of different waveforms is amplified prior to being combined.

5. The method of claim 2, wherein the first phase is a systolic phase of the cardiac cycle.

6. The method of claim 2, wherein the first phase is a sharp upstroke beginning a systolic phase of the cardiac cycle.

7. The method of claim 2, wherein the second phase is a diastolic phase of the cardiac cycle.

8. The method of claim 2, wherein the first frequency corresponds to a highest frequency of a systolic phase of the cardiac cycle.

9. The method of claim 2, wherein the first frequency is a frequency between 3 Hz and 20 Hz.

10. The method of claim 2, wherein the first frequency is approximately 3.2 Hz.

11. The method of claim 2, wherein the second frequency corresponds to a highest frequency of a diastolic phase of the cardiac cycle.

12. The method of claim 2, wherein the second frequency is a frequency between 1.5 Hz and 20 Hz.

13. The method of claim 2, wherein the second frequency is approximately 1.75 Hz.

14. The method of claim 1, wherein the filtering the peripheral pulse waveform to isolate the specific different phases of the cardiac cycle into the plurality of different waveforms including the at least first and second ones of the plurality of different waveforms comprises filtering by a first high pass filter to provide the first one of the plurality of different waveforms and a second high pass filter to provide the second one of the plurality of different waveforms.

15. The method of claim 14, wherein the first high pass filter is of a higher order than the second high pass filter.

16. The method of claim 14, wherein the first high pass filter is a seventh order filter.

17. The method of claim 14, wherein the second high pass filter is a fourth order filter.

18. The method of claim 14, further comprising smoothing the combined waveform using a smoothing filter, wherein the smoothing filter is of a lower order than the first and second high pass filters.

19. The method of claim 1, further comprising smoothing the combined waveform using a smoothing filter.

20. The method of claim 19, wherein the smoothing filter attenuates frequencies above 20 Hz.

21. The method of claim 19, wherein the smoothing filter is a low-pass filter with cut-off frequency of approximately 6 Hz.

22. The method claim 19, wherein the filtering is carried out by a first high pass filter at a first frequency to provide a first filtered waveform and by a second high pass filter at a second frequency to provide a second filtered waveform as the first and second ones of the plurality of different waveforms corresponding to the different phases of a cardiac cycle, wherein the first frequency is associated with a first phase of a cardiac cycle and the second frequency is associated with a second phase of the cardiac cycle, and wherein the smoothing filter is a third order filter.

23. The method of claim 1, wherein the combined waveform is a complete cardiac cycle.

24. The method of claim 23, further comprising obtaining a peripheral systolic blood pressure and a diastolic blood pressure of the subject, and calculating a true mean intra-arterial pressure using the estimated intra-arterial waveform, the peripheral systolic blood pressure and the diastolic blood pressure.

25. The method of claim 24, further comprising calculating an estimated central pressure waveform using the true mean intra-arterial pressure.

26. The method of claim 24, wherein the subject is human.

27. The method of claim 1, wherein one of the at least first and second filters is a Butterworth filter.

28. The method of claim 1, further comprising providing the combined waveform as an output of a signal processing circuit.

29. A method of estimating an intra-arterial waveform of a subject, the method comprising:
obtaining a cuff pressure measurement of a subject;
deriving a peripheral pulse waveform from the obtained cuff pressure measurement;
filtering the peripheral pulse waveform to provide a plurality of filtered waveforms, wherein the filtering is carried out to isolate specific different phases of a cardiac cycle into different filtered waveforms including at least a first filtered waveform corresponding to a first phase of the cardiac cycle and a second filtered waveform corresponding to a different second phase of the cardiac cycle of the subject;
generating a continuous waveform of the cardiac cycle by selectively combining the plurality of filtered waveforms to form different portions of the continuous waveform thereby allow the plurality of filtered waveforms to be recombined without cross-interference; and
estimating the intra-arterial waveform of the subject using the generated continuous waveform of the cardiac cycle,
wherein at least one of the filtering, generating or estimating is carried out using at least one processor.

30. The method of claim 29, wherein the filtering is carried out using at least first and second different filters, the first filter providing the first filtered waveform and the second filter providing the second filtered waveform, wherein the first phase is a systolic phase of the cardiac cycle, and wherein the second phase is a diastolic phase of the cardiac cycle.

31. The method of claim 29, further comprising providing the intra-arterial waveform as an output of a signal processing circuit.

32. The method of claim 29, further comprising determining an intra-arterial mean arterial blood pressure using the estimated intra-arterial waveform and only oscillometric measurements taken from the subject using a cuff measurement device.

33. A method of estimating an intra-arterial waveform of a subject, the method comprising:
deriving a peripheral pulse waveform from one or more oscillometric measurements obtained by a blood pressure cuff;
filtering the peripheral pulse waveform at a first cut-off frequency using a first filter to generate a first waveform corresponding to only a systolic phase of a cardiac cycle of the subject;
filtering the peripheral pulse waveform at a second cut-off frequency using a second filter to generate a second waveform corresponding to only a diastolic phase of the cardiac cycle of the subject, wherein the second cut-off frequency is different from the first cut-off frequency;
amplifying at least one of the first and second waveforms; and then
combining the first waveform and the second waveform to form a combined continuous waveform, wherein the first and second waveforms form different portions of the combined continuous waveform to allow the first and second waveforms to be recombined without cross-interference to generate an estimate of the intra-arterial waveform of the subject.

34. The method of claim 33, further comprising providing the estimate of the intra-arterial waveform as an output of a signal processing circuit.

35. The method of claim 33, further comprising:
calculating an intra-arterial mean arterial blood pressure based on the intra-arterial waveform and oscillometric measurements of the subject; and
providing the intra-arterial mean arterial blood pressure as an output of a signal processing circuit.

36. The method of claim 33, wherein the filtering is carried out to isolate specific different phases of the cardiac cycle, and wherein the method further comprises separately transforming one or more of the first and second waveforms prior to combining the first and second waveforms.

* * * * *